United States Patent
Simpson et al.

(10) Patent No.: US 8,293,509 B2
(45) Date of Patent: *Oct. 23, 2012

(54) ALCOHOL PRODUCTION PROCESS

(75) Inventors: Sean Dennis Simpson, Auckland (NZ); Richard Llewellyn Sydney Forster, Pukekohe (NZ); Matthew James Rowe, Auckland (NZ); Phuong Loan Tran, Auckland (NZ); Christophe Collet, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 142 days.

This patent is subject to a terminal disclaimer.

(21) Appl. No.: 12/529,761

(22) PCT Filed: Mar. 19, 2008

(86) PCT No.: PCT/NZ2008/000054
§ 371 (c)(1),
(2), (4) Date: Jan. 6, 2010

(87) PCT Pub. No.: WO2008/115080
PCT Pub. Date: Sep. 25, 2008

(65) Prior Publication Data
US 2010/0105115 A1    Apr. 29, 2010

(30) Foreign Application Priority Data

Mar. 19, 2007 (NZ) ........................ 553984

(51) Int. Cl.
C12P 7/00 (2006.01)
C12P 7/02 (2006.01)
C12P 7/04 (2006.01)
C12P 7/06 (2006.01)
C12P 7/16 (2006.01)
C12P 1/04 (2006.01)
C12N 1/20 (2006.01)

(52) U.S. Cl. .......... 435/161; 435/41; 435/132; 435/155; 435/157; 435/160; 435/170; 435/252.7

(58) Field of Classification Search ................. None
See application file for complete search history.

(56) References Cited

U.S. PATENT DOCUMENTS
5,173,429 A    12/1992  Gaddy et al.
(Continued)

FOREIGN PATENT DOCUMENTS
EP    0 146 075    8/1989
(Continued)

OTHER PUBLICATIONS

Duncan, Sylvia H, et al.. "Contribution of acetate to butyrate formation by human faecal bacteria." British Journal of Nutrition, 2004, vol. 91, pp. 915-923.

(Continued)

*Primary Examiner* — Chris R Tate
*Assistant Examiner* — Aaron J Kosar
(74) *Attorney, Agent, or Firm* — Frank S Molinaro

(57) ABSTRACT

The invention relates to biological processes for producing one or more desired products, including alcohols such as ethanol and butanol. The processes comprise carrying out first and second fermentations of substrates in first and second bioreactors, wherein each fermentation produces one or more desired products and/or one or more by-products that can be utilized in the other fermentation. A product and/or by-product of the first fermentation is introduced to the second bioreactor during the fermentation, and a product and/or by-product of the second fermentation is introduced to the first bioreactor during the fermentation.

16 Claims, 7 Drawing Sheets

U.S. PATENT DOCUMENTS

| | | | |
|---|---|---|---|
| 5,593,886 | A | 1/1997 | Gaddy |
| 5,753,474 | A | 5/1998 | Ramey |
| 5,807,722 | A | 9/1998 | Gaddy |
| 5,821,111 | A | 10/1998 | Grady et al. |
| 6,136,577 | A | 10/2000 | Gaddy |
| 6,306,638 | B1 | 10/2001 | Yang et al. |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| RE39,175 | E | 7/2006 | Gaddy et al. |
| 7,196,218 | B2 | 3/2007 | Gaddy et al. |
| 7,285,402 | B2 | 10/2007 | Gaddy et al. |
| 2003/0106437 | A1 | 6/2003 | Pajunen et al. |
| 2003/0211585 | A1 | 11/2003 | Gaddy et al. |
| 2006/0051848 | A1 | 3/2006 | Nishio et al. |
| 2007/0275447 | A1 | 11/2007 | Lewis et al. |
| 2009/0203100 | A1* | 8/2009 | Simpson et al. ............ 435/161 |
| 2009/0275787 | A1* | 11/2009 | Forster et al. ............ 568/903 |
| 2010/0105115 | A1* | 4/2010 | Simpson et al. ............ 435/135 |
| 2010/0317074 | A1* | 12/2010 | Simpson et al. ............ 435/140 |
| 2010/0323417 | A1* | 12/2010 | Simpson et al. ............ 435/157 |

FOREIGN PATENT DOCUMENTS

| | | |
|---|---|---|
| EP | 0 125 983 | 1/1990 |
| WO | WO 2008/028055 | 3/2008 |
| WO | WO 2008/154301 | 12/2008 |
| WO | WO 2009/020747 | 2/2009 |

OTHER PUBLICATIONS

Qureshi, Nasib, et al. "High-Productivity Continuous Biofilm Reactor for Butanol Production." Applied Biochemistry and Biotechnology, vol. 113-116, 2004. pp. 713-721.

Chen, Chih-Kuang, et al. "Effect of Acetate on Molecular and Physiological Aspects of *Clostridium beijerinckii* NCIMB 8052 Solvent Production and Strain Degeneration." 1999. Applied and Environmental Microbiology, Feb. 1999, vol. 65, No. 2, pp. 499-505.

Phillips et al. "Synthesis gas as substrate for the biological production of fuels and chemicals", 1994. Applied Biochemistry and Biotechnology, 45(1), pp. 145-157.

Abrini et al. "*Clostridium autoethanogenum*, sp. Nov., an anaerobic bacterium that produces ethanol from carbon monoxide", 1994. Archives of Microbiology, 161(4), pp. 345-351.

Ragsdale, Stephen. "Life with Carbon Monoxide." 2004. Critical Reviews in Biochemistry and Molecular Biology, pp. 165-195.

Henstra, Anne M. "Microbiology of synthesis gas fermentation for biofuel production." 2007, vol. 18, pp. 200-206.

Grethlein, et al. "Evidence for Production of n-Butanol from Carbon Monoxide by *Butyribacterium methylotrophicum*", Journal of Fermentation and Bioengineering, 1991. Journal of Fermentation and Bioengineering, 72(1), pp. 58-60.

Claassen, et al. "Utilisation of biomass for the supply of energy carriers", 1999. Applied Microbiology and Biotechnology, 52(6), pp. 741-755.

\* cited by examiner

FIGURE 5

| START | | END | | | | | | |
|---|---|---|---|---|---|---|---|---|
| Acetate [g/l] | Butyrate [g/l] | Acetate [g/l] | Butyrate [g/l] | Ethanol [g/l] | Butanol [g/l] | H2 [psig] | CO2 [psig] | N2 [psig] |
| 0.0 | 0.0 | 2.3 | 3.4 | 0.7 | 0.6 | 13.8 | 16.8 | 5.0 |
| 0.0 | 0.8 | 2.7 | 3.9 | 0.8 | 1 | 14.5 | 17.5 | 4.9 |
| 0.0 | 1.6 | 2.5 | 4.3 | 0.8 | 1.3 | 14.4 | 16.4 | 4.3 |
| 0.0 | 2.3 | 2.7 | 5 | 0.8 | 1.5 | 16.7 | 18.6 | 4.3 |
| 1.0 | 0.7 | 2.3 | 3.8 | 0.6 | 1.3 | 14.5 | 16.5 | 4.2 |
| 2.6 | 2.1 | 5 | 5.5 | 0.6 | 1.5 | 18.6 | 18.9 | 3.6 |

FIGURE 6

| START | | END | | | | |
|---|---|---|---|---|---|---|
| Gas partial pressure | | Gas partial pressure | | | Acetate specific production [g / g CDW] | Ethanol specific production [g / g CDW] |
| H2 [psig] | CO2 [psig] | H2 [psig] | CO [psig] | CO2 [psig] | | |
| 0.0 | 2.5 | 0.0 | 1.0 | 8.0 | 7.1 | 1.2 |
| 2.9 | 2.3 | 2.2 | 0.2 | 8.6 | 8 | 2.5 |
| 4.2 | 2.2 | 3.5 | 0.3 | 8.5 | 12.6 | 5.9 |
| 4.9 | 2.4 | 4.4 | 0.1 | 8.4 | 8.8 | 4.1 |
| 6.1 | 2.4 | 4.8 | 0.2 | 8.1 | 14.5 | 4.7 |

Note: START Gas partial pressure also includes CO column with values 7.8, 7.6, 7.2, 7.9, 8.3.

FIGURE 7

| H2 [%] | CO [%] | CO2 [%] | Butyrate specific production [g / g CDW] |
|---|---|---|---|
| 0 | 95 | 5 | 1.9 |
| 20 | 20 | 8 | 4.8 |

ALCOHOL PRODUCTION PROCESS

CROSS-REFERENCE TO RELATED APPLICATIONS

This application is the National Stage of International Application No. PCT/NZ2008/000054, filed on Mar. 19, 2008, which claims the benefit of New Zealand Application Serial No. 553984, filed on Mar. 19, 2007, the contents of both of the foregoing applications are hereby incorporated by reference in their entirety.

FIELD OF THE INVENTION

This invention relates generally to methods for increasing the productivity of processes of making products by microbial fermentation of gases and carbohydrates. It more particularly relates to processes for the production of alcohols, more particularly ethanol and butanol, by fermentation of gaseous substrates containing carbon monoxide and fermentation of carbohydrate substrates.

BACKGROUND OF THE INVENTION

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Two alcohols useful in biofuels are ethanol and butanol.

Ethanol is rapidly becoming a major hydrogen-rich liquid transport fuel around the world. Worldwide consumption of ethanol in 2002 was an estimated 10.8 billion gallons. The global market for the fuel ethanol industry has also been predicted to grow sharply in future, due to an increased interest in ethanol in Europe, Japan, the USA and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union (EU) to set member nations a mandated target for the consumption of sustainable transport biofuels.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as their sole carbon source was first discovered in 1903. This was later determined to be a property of organisms that use the acetyl coenzyme A (acetyl CoA) biochemical pathway of autotrophic growth (also known as the Woods-Ljungdahl pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Aribini et al, *Archives of Microbiology* 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to Green House Gas emissions.

Butanol may be used as a fuel in an internal combustion engine. It is in several ways more similar to gasoline than it is to ethanol. Butanol can be produced by fermentation of biomass. The process uses the bacterium from the genus *Clostridium* (such as *Clostridium acetobutylicum*). It was Chaim Weizmann who first used this bacterium for the production of acetone from starch (with the main use of acetone being the making of Cordite) in 1916. Butanol was a by-product of this fermentation. The process also creates recoverable amounts of ethanol, $H_2$ and $CO_2$ gases and a number of other by-products: acetic, lactic and propionic acids, acetone and isopropanol. Indeed, processes for producing butanol by fermentation are now widely referred to as Acetone Butanol Ethanol (ABE) processes, to reflect three of the principal products of this fermentation.

The ABE process was an industry standard until the late 1940s, when low oil costs drove more efficient processes based on hydrocarbon cracking and petroleum distillation techniques.

More recently, as interest in the production and application of environmentally sustainable fuels has strengthened, interest in biological processes to produce butanol (often referred to as bio-butanol) has increased. For example, in Jun. 2006 BP announced collaboration with Dupont and British Sugar to manufacture biobutanol using conventional technology in the UK. BP provides a route for butanol into the transport fuel market and has stated that it aims to blend butanol with petrol at its 1200 filling stations.

It is an object of the present invention to go at least some way towards providing a process of producing alcohols by fermentation of gaseous substrates and carbohydrate substrates that has increased efficiency over prior art processes, or at least to offer the public a useful choice.

SUMMARY OF THE INVENTION

In a first, broad aspect, the present invention provides a process for producing one or more desired products, the process comprising carrying out first and second fermentations of substrates in first and second bioreactors, wherein each fermentation produces one or more desired products and/or one or more by-products that can be utilised in the other fermentation, and the process further comprising the steps of (a) introducing one or more products and/or by-products of the first fermentation that can be utilised by the second fermentation into the second bioreactor during the fermentation, and (b) introducing one or more products and/or by-products of the second fermentation that can be utilised by the first fermentation into the first bioreactor during the fermentation.

In another aspect, the present invention provides a biological process for producing one or more desired products selected from alcohols and by-products of fermentation processes that produce alcohols, the process comprising carrying out a first fermentation of gaseous substrates in a first bioreactor, and a second fermentation of carbohydrate-containing substrates in a second bioreactor, wherein each fermentation produces one or more desired products and/or by-products that can be utilised in the other fermentation, and the process further comprising the steps of (a) introducing one or more products and/or by-products of the first fermentation that can be utilised by the second fermentation into the second bioreactor during the fermentation, and (b) introducing one or more products and/or by-products of the second fermentation that can be utilised by the first fermentation into the first bioreactor during the fermentation.

In a further aspect, the present invention provides a biological process for producing ethanol, the process comprising carrying out a first fermentation of gaseous substrates in a first bioreactor, and a second fermentation of carbohydrate-containing substrates in a second bioreactor, wherein each fermentation produces ethanol or butanol or both, and one or more by-products that can be utilised in the other fermentation, and at least one fermentation produces ethanol, and the process further comprising the steps of (a) introducing one or more by-products of the first fermentation that can be utilised by the second fermentation into the second bioreactor during the fermentation, (b) introducing one or more by-products of the second fermentation that can be utilised by the first fermentation into the first bioreactor during the fermentation; and (c) recovering ethanol from one or both fermentations.

In preferred embodiments, both fermentations produce ethanol and ethanol is recovered from both fermentations.

In preferred embodiments, either or both fermentations produce butanol in addition to ethanol, and the process further comprises recovering butanol from the fermentation(s).

In a further aspect, the present invention provides a biological process for producing butanol, the process comprising carrying out a first fermentation of gaseous substrates in a first bioreactor, and a second fermentation of carbohydrate-containing substrates in a second bioreactor, wherein each fermentation produces butanol or ethanol or both, and one or more by-products that can be utilised in the other fermentation, and at least one of the fermentations produces butanol, and the process further comprising the steps of (a) introducing one or more by-products of the first fermentation that can be utilised by the second fermentation into the second bioreactor during the fermentation, (b) introducing one or more by-products of the second fermentation that can be utilised by the first fermentation into the first bioreactor during the fermentation; and (c) recovering butanol from one or both fermentations.

In preferred embodiments, both fermentations produce butanol and butanol is recovered from both fermentations.

In preferred embodiments, either or both fermentations produce ethanol in addition to butanol, and the process further comprises recovering ethanol from the fermentation(s).

In a further aspect, the present invention provides a process for producing one or more desired products selected from alcohols and by-products of fermentation processes that produce alcohols, the process comprising the following steps, in any order:
  (a) in a first bioreactor, carrying out a first fermentation process comprising fermenting a gaseous substrate comprising carbon monoxide to produce reaction products comprising acetate and/or butyrate;
  (b) introducing acetate and/or butyrate obtained from the first fermentation into a second bioreactor;
  (c) in the second bioreactor, fermenting a carbohydrate-containing substrate to produce reaction products comprising one or more alcohols and hydrogen and carbon dioxide gases;
  (d) introducing hydrogen or carbon dioxide, or both, obtained from the second fermentation into the first bioreactor during the first fermentation.

In certain embodiments, step (a) produces reaction products comprising one or more alcohols and acetate and/or butyrate.

In certain embodiments, the desired products comprise ethanol. In other embodiments, the desired products comprise butanol. In certain preferred embodiments, the desired products comprise both ethanol and butanol.

In a further aspect, the present invention provides a process for producing ethanol, the process comprising the following steps, in any order:
  (a) in a first bioreactor, carrying out a first fermentation comprising fermenting a gaseous substrate comprising carbon monoxide to produce reaction products comprising ethanol and acetate;
  (b) introducing acetate obtained from the first fermentation process into a second bioreactor;
  (c) in the second bioreactor, carrying out a second fermentation comprising fermenting a carbohydrate-containing substrate to produce reaction products comprising butanol, ethanol, and hydrogen and carbon dioxide gases;
  (d) introducing hydrogen gas or carbon dioxide, or both, obtained from the second fermentation process into the first bioreactor during the first fermentation process; and
  (e) recovering ethanol from the first fermentation or second fermentation or both.

In preferred embodiments, ethanol is recovered from both fermentations. In certain embodiments, the process further includes recovering butanol from the second fermentation. In certain embodiments, the process includes recovering butanol and ethanol from the second fermentation as a mixed alcohol stream.

In certain embodiments, the first fermentation is carried out by one or more strains of anaerobic acetogenic bacteria in a liquid nutrient medium. In certain embodiments, the acetogenic bacterium is selected from *Clostridium, Moorella, Oxobacter, Peptostreptococcus, Acetobacterium, Eubacterium, Desulfotomaculum, Archaeglobulus* and *Butyribacterium*. In one preferred embodiment, the acetogenic bacterium is *Clostridium autoethanogenum*.

In certain embodiments, the second fermentation is carried out by one or more bacteria of the genus *Clostridium*. In one embodiment, the bacterium is *Clostridium acetobutylicum*.

In a further aspect, the present invention provides a process for producing butanol, the process comprising the following steps, in any order:
(a) in a first bioreactor, carrying out a first fermentation comprising fermenting a gaseous substrate comprising carbon monoxide to produce reaction products comprising butanol and butyrate;
(b) introducing butyrate obtained from the first fermentation process into a second bioreactor;
(c) in the second bioreactor, carrying out a second fermentation comprising fermenting a carbohydrate-containing substrate to produce reaction products comprising butanol, ethanol, and hydrogen and carbon dioxide gases;
(d) introducing hydrogen gas or carbon dioxide, or both, obtained from the second fermentation process into the first bioreactor during the first fermentation process; and
(e) recovering butanol from the first fermentation or second fermentation or both.

In preferred embodiments, butanol is recovered from both fermentations. In certain embodiments, the process further includes recovering ethanol from the first or second fermentation. In certain embodiments, the process includes recovering butanol and ethanol from the first or second fermentation as a mixed alcohol stream.

In certain embodiments, the first fermentation is carried out by one or more strains of *Clostridium, Oxobacter, Peptostreptococcus, Acetobaterium, Eubacterium, Butyribacterium, Moorella, Desulfotomaculum*, and *Archaeoglobus* bacteria in a liquid nutrient medium. In a preferred embodiment, the bacterium is *Clostridium tetanomorphum*.

In certain embodiments, the second fermentation is carried out by one or more bacteria of the genus *Clostridium*. In a preferred embodiment, the bacterium is *Clostridium acetobutylicum*.

In certain embodiments, ethanol, butanol, acetate and/or butyrate are continuously recovered from the first bioreactor and recovered acetate and/or butyrate are continuously introduced into the second bioreactor.

In certain embodiments, the recovery of ethanol, butanol, acetate and/or butyrate comprises continuously removing a portion of fermentation broth from the bioreactor and recovering separately ethanol, butanol, acetate and/or butyrate from the removed portion of the broth.

In certain embodiments the recovery of ethanol, butanol, acetate and/or butyrate includes passing the removed portion of the broth containing ethanol, butanol, acetate and/or butyrate through a separation unit to separate bacterial cells from the ethanol, butanol, acetate and/or butyrate, to produce a cell-free ethanol-, butanol-, acetate- and/or butyrate-containing permeate, and returning the bacterial cells to the first bioreactor.

In the above embodiments, the recovery of ethanol, butanol, acetate and/or butyrate preferably includes first removing ethanol and/or butanol from the cell-free permeate followed by removing acetate and/or butyrate from the cell-free permeate, then returning the cell-free permeate to the first bioreactor.

In certain embodiments, the gaseous substrate is a waste gas obtained from an industrial process. In certain embodiments, the industrial process is selected from the group consisting of ferrous metal products manufacturing, non-ferrous products manufacturing, petroleum refining processes, gasification of biomass, gasification of municipal waste, gasification of coal, electric power production, carbon black production, ammonia production, methanol production and coke manufacturing. In other embodiments, the gaseous substrate may comprise automobile exhaust fumes.

In certain embodiments, the gaseous substrate contains less than about 15% $H_2$ by volume, such as less than about 10% $H_2$, such as less than about 5% $H_2$.

In certain embodiments, the gaseous substrate comprises about 70% CO to about 95% CO by volume.

In certain embodiments, the reaction products of the second fermentation include ethanol, butanol, acetate, butyrate, acetone, hydrogen and carbon dioxide.

In certain embodiments, step (d) comprises introducing hydrogen obtained from the second fermentation into the first fermentation. In certain embodiments, step (d) comprises introducing both carbon dioxide and hydrogen obtained from the second fermentation into the first fermentation.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which:

FIG. 5: Production of various products by *C. acetobutylicum* when butyrate or acetate and butyrate are added to the reaction (fermentation 2). Spiking of Butyrate or Acetate and Butyrate mixture in a 50 ml culture of *C. acetobutylicum* 824 growing on 50 g/l glucose, initial pH 7.3, in 234 ml serum bottle. Headspace (184 ml): 100% N2.

FIG. 6: Production of acetate and ethanol by *C. autoethanogenum* when hydrogen is added to the reaction (fermentation 1). Spiking of Hydrogen gas in a 50 ml culture of *C. autoethanogenum* growing at pH 5.5. Initial composition of the 184 ml headspace: 30 psig overpressure of a gas mixture made of 17% CO, 5% $CO_2$ and increasing amounts of H2 from 0% (Hydrogen partial pressure of 0.0 psig) to 13.7% (Hydrogen partial pressure of 6.1 psig); and, FIG. 7: Production of butyrate by *C. tetanomorphum* when hydrogen is added to the reaction (fermentation 1). *Clostridium tetanomorphum* (DSM 528) growing on 50 ml Media LM23+1 g/l Yeast extract with a 184 ml headspace, 30 psig overpressure containing Carbon monoxide, Carbon Dioxide in presence or absence of Hydrogen.

DETAILED DESCRIPTION OF THE INVENTION

Definitions

Figure 1:
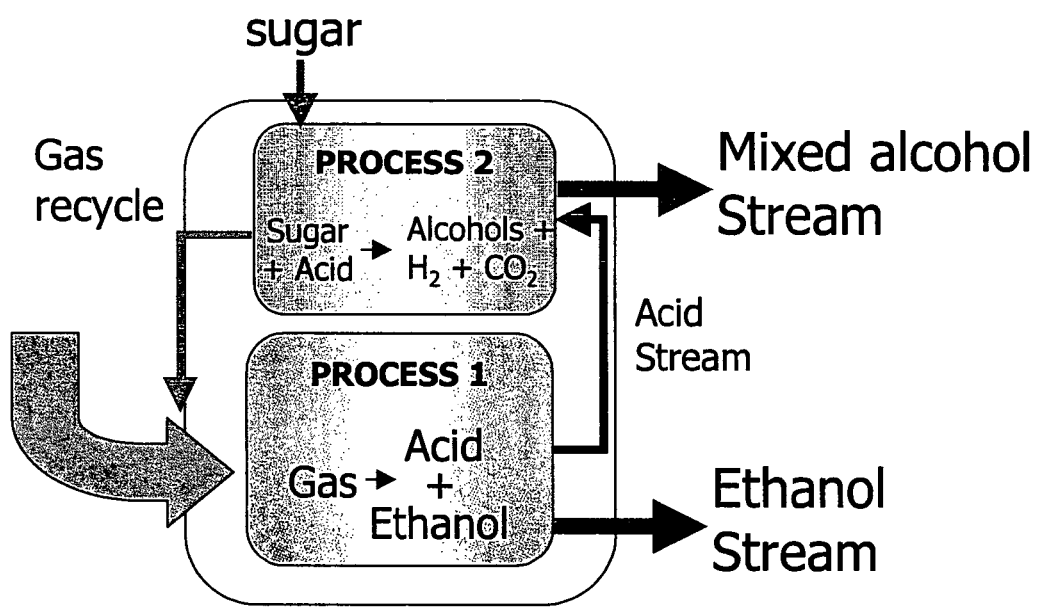
FIG. 1: A schematic of an example of an integrated process according to the present invention for producing mixed alcohols and ethanol, by fermentation of gaseous substrates containing carbon monoxide (fermentation 1) and fermentation of carbohydrate substrates (fermentation 2).

Unless otherwise defined, the following terms as used throughout this specification are defined as follows:

The term "acetate" includes both acetate salt alone and a mixture of molecular or free acetic acid and acetate salt, such as the mixture of acetate salt and free acetic acid present in a fermentation broth as described herein. The ratio of molecular acetic acid to acetate in the fermentation broth is dependent upon the pH of the system.

The term "butyrate" includes both butyrate salt alone and a mixture of molecular or free butyric acid and butyrate salt, such as the mixture of butyrate salt and free butyric acid present in a fermentation broth as described herein. The ratio of molecular butyric acid to butyrate in the fermentation broth is dependent upon the pH of the system.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact.

The term "mixed alcohols" or "alcohols" includes but is not limited to butanol, ethanol, and isopropanol present in a fermentation broth as described herein.

The terms "increasing the efficiency", "increased efficiency" and the like, when used in relation to a fermentation process, include, but are not limited to, increasing one or more of the rate of growth of microorganisms catalysing the fermentation, the volume of desired product (such as alcohols) produced per volume of substrate (such as sugar) consumed, the rate of production or level of production of the desired product, and the relative proportion of the desired product produced compared with other by-products of the fermentation.

The term "co-substrate" refers to a substance that while not being the primary energy and material source for product synthesis, can be utilised for product synthesis when added in addition to the primary substrate.

The term "gaseous substrate" is used in a non-limiting sense to include substrates containing or derived from one or more gases.

The term "limiting concentration" means an initial concentration of a given component in a microbial fermentation medium that is sufficiently low to ensure that it will be depleted at an early stage in the fermentation.

General Methodology

In broad terms, the present invention relates to biological processes for producing products (preferably alcohols such as butanol and/or ethanol) and/or desired by-products of such processes (such as acetone, acetate, butyrate) involving two fermentations in separate bioreactors. The two fermentations are linked by introducing one or more products and/or by-products of each fermentation into the other fermentation. The products and/or by-products introduced into each fermentation include substances that can be utilised by that fermentation, for example as a co-substrate for the micro-organisms carrying out the fermentation, and therefore have a beneficial effect on the fermentation. Accordingly, the processes of the present invention, at least in preferred embodiments, have an increased efficiency when compared with the individual fermentations performed separately. As will be apparent depending on the particular reactions involved, the products and by-products will vary. Furthermore, a by-product of one reaction may be a product of another and vice versa. Thus "product" and "by-product" are used in a non-limiting sense.

The following description focuses on embodiments in which each fermentation produces one or more alcohols (such as ethanol and butanol) and one or more by-products (such as acetate, butyrate, carbon dioxide and hydrogen) however, the invention is not limited thereto. By way of example, in one preferred embodiment, alcohol is only or substantially only produced in one of the fermentations (for example, the first fermentation may produce butyrate but no or substantially no butanol).

Methods for producing desired products including alcohols by fermentation of sugars and other substrates, including gaseous substrates containing CO, are known in the art. For example, many micro-organisms are capable of fermenting $C_5$ and/or $C_6$ sugars to produce fermentation products such as ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid and tartaric acid, and amino acids such as L-glutaric acid, L-lysine, L-aspartic acid, L-trypophan, L-arylglycines or salts of any of these acids. Microorganisms that can be used in such fermentation processes can include, for example, yeasts such as *Klyveromyces* species, *Candida* species, *Pichia* species, *Brettanomyces* species, *Saccharomyces* species such as *Sarrachormyces cerevisiae* and *Saccharomyces uvarum*, *Hansenula* species and *Pachysolen* species. Alternatively, the microorganism can be a bacterial species such as *Clostridium*, *Leuconostoc*, *Enterobacter*, *Klebsiella*, *Erwinia*, *Serratia*, *Lactococcus*, *Pediococcus*, *Acetobacter*, *Gluconobacter*, *Lactobacillus*, *Aspergillus*, *Propionibacterim*, *Rhizopus*, *Zymomonas mobilis*, *Moorella*, *Eubacterium*, *Oxobacter*, *Butyribacterium*, *Desulfotomaculum*, *Archaeoglobus*, and *Peptostreptococcus*.

In preferred embodiments of the present invention, the first fermentation involves fermenting a gaseous substrate comprising carbon monoxide to produce one or more desired products, preferably ethanol and/or butanol. In one embodiment, the first fermentation preferably produces acetate as a by-product in addition to the alcohol(s), and can also utilise hydrogen or carbon dioxide, or both, as a co-substrate in the fermentation. In another embodiment, the first fermentation produces butyrate as a by-product in addition to the alcohol(s), and can also utilise hydrogen or carbon dioxide, or both, as a co-substrate in the fermentation. In another embodiment, both acetate and butyrate are produced in the first fermentation.

The second fermentation involves fermenting a carbohydrate-containing substrate to produce reaction products comprising one or more alcohols (preferably mixed alcohols including ethanol and butanol). The second fermentation can also use a by-product of the first fermentation as a co-substrate, for example acetate and/or butyrate. The second fermentation preferably also produces hydrogen and carbon dioxide as gaseous by-products.

In the above embodiments, the process of the invention involves introducing acetate and/or butyrate produced by the first fermentation into the second fermentation process, in which alcohols, hydrogen and carbon dioxide are produced from sugars. The acetate and/or butyrate can be utilised in the second fermentation, thereby increasing its efficiency. Without wishing to be bound by theory, it is believed that in this fermentation the acetate and/or butyrate is taken up by the organism and converted to a biochemical precursor of alcohol production. The hydrogen and/or carbon dioxide by-product of the mixed alcohol fermentation is also introduced into the first fermentation process. The introduced hydrogen and/or carbon dioxide gas is then used as a co-substrate by the microorganisms performing the fermentation, thereby increasing the efficiency of the first fermentation as well.

An example of one embodiment of the present invention is illustrated in general schematic form in FIG. 1. In this figure, Reaction 1 is the conversion of carbon monoxide-containing gas from a steel mill to ethanol and acetate, and Reaction 2 is the conversion of carbohydrate sugars and the acetate by-product from Reaction 1, to an alcohol or a mixture of alcohols and hydrogen and carbon dioxide gases. Gas, produced by Reaction 2, is then introduced back into Reaction 1. One or a mixture of alcohols, including ethanol and butanol for example, are recovered as the desired end-products of the integrated process.

The process of the invention has particular applicability to the production of ethanol and/or butanol from gaseous substrates in which the level of hydrogen is relatively low, such as automobile exhaust gases and high volume CO-containing industrial flue gases. Examples include gases produced during ferrous metal products manufacturing, non-ferrous products manufacturing, petroleum refining processes, gasification of coal, electric power production, carbon black production, ammonia production, methanol production and coke manufacturing.

The present invention, by producing its own source of hydrogen (as a by-product of the second fermentation) enables such gaseous substrates to be used to produce ethanol and/or butanol by anaerobic fermentation, without the need to obtain hydrogen from another source. Also, because acetate (and/or butyrate) produced as a by-product of the fermentation is used as a co-substrate to increase the efficiency of the second fermentation that also produces desired alcohol products, the invention avoids the need to develop solutions for disposal of the by-product(s).

First Fermentation

A number of anaerobic bacteria are known to be capable of carrying out the fermentation of CO to ethanol and acetic acid and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, and *Clostridium autoethanogenum* (Aribini et al, *Archives of Microbiology* 161: pp 345-351). Other suitable bacteria include those of the genus *Moorella*, including *Moorella* sp HUC22-1, (Sakai et al, *Biotechnology Letters* 29: pp 1607-1612). The disclosures of each of these publications are fully incorporated herein by reference. In addition, other acetogenic anaerobic bacteria may be selected by a person of skill in the art including, for example, bacteria of the genera *Oxobacter, Peptostreptococcus, Acetobacterium, Eubacterium, Desulfotomaculum, Archaeglobulus* and *Butyribacterium*.

One preferred micro-organism suitable for use in the present invention is *Clostridium autoethanogenum* that is available commercially from the Deutsche Sammlung von Mikroorganismen und Zellkulturen GmbH (DSMZ) and having the identifying characteristics of DSMZ deposit number DSMZ 10061.

A number of anaerobic bacteria are known to be capable of carrying out the fermentation of CO to butyrate or butanol and butyrate and are suitable for use in the process of the present invention. Examples of such bacteria include those of the genus *Clostridium, Oxobacter, Peptostreptococcus, Acetobaterium, Eubacterium, Butyribacterium, Moorella, Desulfotomaculum*, and *Archaeoglobus*, including those described in Henstra et al, 2007 (Current Opinion in Biotechnology 2007, 18:200-206); for example, *Clostridium carboxidivorans, Butyribacterium methylotrophicum, Clostridium tetanomorphum, Clostridium autoethanogenum, Clostridium ljungdahlii, Clostridium carboxidivorans, Clostridium tetanomorphum, Oxobacter pfennigii, Peptostreptococcus productus, Acetobacterium woodii, Eubacterium limosum, Butyribacterium methylotrophicum, Moorella thermoacetica, Moorella thermoautotrophica, Desulfotomaculum kuznetsovii, Desulfotomaculum thermobenzoicum*, and *Archaeoglobulus fulgidis*. In a preferred embodiment, the bacterium is *Clostridium tetanomorphum*. Persons of skill in the art to which the invention relates may appreciate additional bacteria of use in this embodiment of the invention.

It should be appreciated that a mixed culture of two or more bacteria may be used in the first fermentation.

Culturing of the bacteria used in the first fermentation may be conducted using any number of processes known in the art for culturing and fermenting substrates using anaerobic bacteria. However, by way of example, those process generally described in the following articles using gaseous substrates for fermentation may be utilised in the present invention: K. T. Masson, M. D. Ackerson, E. C. Clausen and J. L. Gaddy (1991). Bioreactors for synthesis gas fermentations resources. Conservation and Recycling, 5; 145-165; K. T. Klasson, M. D. Ackerson, E. C. Clausen and J. L. Gaddy (1991). Bioreactor design for synthesis gas fermentations. Fuel. 70. 605-614; K. T. Klasson, M. D. Ackerson, E. C. Clausen and J. L. Gaddy (1992). Bioconversion of synthesis gas into liquid or gaseous fuels. Enzyme and Microbial Technology. 14; 602-608; J. L. Vega, G. M. Antorrena, E. C. Clausen and J. L. Gaddy (1989). Study of Gaseous Substrate Fermentation: Carbon Monoxide Conversion to Acetate. 2. Continuous Culture. Biotech. Bioeng. 34. 6. 785-793; J. L. Vega, E. C. Clausen and J. L. Gaddy (1989). Study of gaseous substrate fermentations: Carbon monoxide conversion to acetate. 1. Batch culture. Biotechnology and Bioengineering. 34. 6. 774-784; J. L. Vega, E. C. Clausen and J. L. Gaddy (1990). Design of Bioreactors for Coal Synthesis Gas Fermentations. Resources, Conservation and Recyling. 3. 149-160; and, Grethlein et al (1991). Evidence for production of n-Butanol from Carbon Monoxide by *Butyribacterium methylotrophicum*. 71. 1. 58-60.

As described above, in a preferred embodiment the carbon source for the first fermentation reaction is a gaseous substrate comprising CO. The gaseous substrate may be a CO-containing waste gas obtained from an industrial process. In certain embodiments, the industrial process is selected from the group consisting of ferrous metal products manufacturing, non-ferrous products manufacturing, petroleum refining processes, gasification of coal, electric power production, carbon black production, ammonia production, methanol production and coke manufacturing. Depending on the composition of the gaseous substrate, it may be desirable to treat it to remove any undesired impurities, such as sub-micron dust particles before introducing it to the fermentation. For example, the gaseous substrate may be filtered or scrubbed using known methods.

Alternatively, in other embodiments of the invention, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

It is generally preferred that the CO-containing gaseous substrate contains a major proportion of CO, and more preferably at least about 70% to about 95% CO by volume. However, in one embodiment it could contain from 15% to about 95% CO by volume. It is not necessary for the gaseous substrate to contain any hydrogen. The gaseous substrate also preferably contains some $CO_2$, such as about 1% to about 30% by volume, such as about 5% to about 10% $CO_2$.

It will be appreciated that for growth of the bacteria and CO-to-alcohol and/or acid fermentation to occur, in addition to the CO-containing substrate gas, a suitable nutrient medium will need to be fed to the bioreactor. Skilled persons will readily appreciate appropriate nutrient media of use in the invention. However, briefly, a nutrient medium will contain vitamins and minerals sufficient to permit growth of the microorganism used. Anaerobic media suitable for the fermentation of ethanol using CO as the sole carbon source are known in the art. For example, suitable media are described in U.S. Pat. Nos. 5,173,429 and 5,593,886 and WO 02/08438 referred to above. Other suitable media are described herein after.

The fermentation should desirably be carried out under appropriate conditions for the CO-to-alcohol and/or acid fermentation to occur. Reaction conditions that should be considered include pressure, temperature, gas flow rate, liquid flow rate, media pH, media redox level, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of alcohol. This in turn means that the retention time (defined as the liquid volume in the bioreactor divided by the input gas flow rate) can be reduced when bioreactors are maintained at elevated pressure rather than atmospheric pressure.

Also, since a given CO-to-alcohol and/or acid conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, ie bioreactors operated at 10 atmospheres of pressure need only be one tenth the volume of those operated at 1 atmosphere of pressure.

The benefits of conducting a gas-to-alcohol fermentation at elevated pressures have been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations, performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the alcohol product is consumed by the culture.

Second Fermentation

As outlined above, in preferred embodiments, the process of the present invention involves recycling of the acetate by-product of the CO-to-ethanol fermentation, and/or the butyrate by-product of CO-to-butanol fermentation, by using them as an additional co-substrate in a second fermentation in which alcohols are produced from carbohydrates. In doing so the acetate and/or butyrate by-product serves to increase the volume of alcohols that can be produced per volume of carbohydrate consumed. A by-product of this reaction is the production of $H_2$ and/or $CO_2$ gases. These gases ($H_2$ and/or $CO_2$) are then introduced into the first fermentation bioreactor, for use as a substrate by the fermentation micro-organisms to increase the efficiency of alcohol production.

In one embodiment, the second fermentation is one that produces ethanol. In particularly preferred embodiments, the second fermentation is one that produces butanol. In another preferred embodiment, the second fermentation produces a mixture of alcohols, including butanol and ethanol. In certain embodiments, the second fermentation is a fermentation in which three of the products include acetone, butanol and ethanol. Such processes are known in the art, and are also referred to as Acetone Butanol Ethanol (ABE) processes, or the Weizmann Process (after Chaim Weizmann who first developed such a process during World War I). Briefly, these processes involve fermenting a suitable fermentable carbohydrate-containing feedstock (such as molasses sugars or sugars derived from other sources) in a suitable nutrient medium in the presence of *Clostridium* microorganisms which convert the sugar to a solvent mixture containing butanol, ethanol and acetone.

A number of species of Clostridia are suitable for use in ABE fermentations. These include, but are not limited to, *Clostridium acetobutylicum*, *Clostridium butylicum*, *Clostridium formicaceticum*, *Clostridium aerotolerans*, *Clostridium cellulolyticum*, *Clostridium thermocellum*, *Clostridium butyricum* and *Clostridium beijerincki*. It will also be appreciated that mixed cultures of two or more different species of bacteria may be used. In a preferred embodiment the bacteria is *Clostridium acetobutylicum*, for example *C. acetobutylicum* P262. It is noted that *Clostridium acetobutylicum* P262 may also be known as *C. saccharobutylicum* (for example *C. saccharobutylicum* DSM 13864, DSMZ, Germany).

Culturing of bacteria used in the second fermentation of the invention may be conducted using any number of processes known in the art for culturing and fermenting carbohydrate containing substrates using anaerobic bacteria. Examples are also provided herein after.

As described above, the second fermentation also produces carbon dioxide and/or hydrogen gases. In the process of the present invention, either one or both of these gases (preferably hydrogen or a mixture of carbon dioxide and hydrogen) is recycled back into the first fermentation. This is exemplified in FIG. 1. Acetate and/or butyrate by-product is recovered from the first fermentation and introduced into the second fermentation. This in turn increases the efficiency of the second fermentation.

Without wishing to be bound by any theory, the uptake of acids such as acetate from the medium has been shown to be directly coupled to the production of alcohol via acetoacetyl-coenzyme A (CoA): acetate/butyrate:CoA-transferase (CoA-transferase). CoA-transferases activate carboxylic acids to the respective CoA thioester at the expense of the CoA thioester of another species of carboxylic acid. Thus, the mechanism of acid utilization by means of the CoA-transferase is energetically favorable because the energy of the thioester bond is conserved and transferred to the acids without the requirement for ATP hydrolysis. CoA-transferases show relatively broad substrate specificities, but each enzyme has characteristic preferred substrates. The uptake of acids by the CoA-transferases of *Clostridium acetobutylicum* serves as a detoxification mechanism by reducing the inhibitory effects of acids on cell growth.

Reactors

The first and second fermentations may be carried out in any suitable bioreactor, such as a continuous stirred tank reactor (CTSR), a bubble column reactor (BCR) or a trickle bed reactor (TBR). Also, in some preferred embodiments of the invention, the bioreactor may comprise a first, growth reactor in which the micro-organisms are cultured, and a second, fermentation reactor, to which broth from the growth reactor is fed and in which most of the fermentation product (ethanol and acetate, for example) is produced.

Product Recovery

The first and second fermentations will result in fermentation broths comprising one or more desirable products (such as ethanol and butanol) and/or one or more by-products (such as acetate and butyrate), as well as bacterial cells, in a nutrient medium.

An alcohol, such as ethanol or butanol, or a mixed alcohol stream containing ethanol and butanol for example, may be recovered from the fermentation broth by methods known in the art, such as fractional distillation or evaporation, pervaporation, and extractive fermentation. By-products such as acetate and butyrate may also be recovered from the fermentation broth using methods known in the art. For example, an adsorption system involving an activated charcoal filter or electrodialysis may be used.

Exemplary methods for the recovery of products and/or by-products of the invention include those described in PCT/NZ2007/000072, U.S. Pat. No. 6,340,581, U.S. Pat. No. 6,136,577, U.S. Pat. No. 5,593,886, U.S. Pat. No. 5,807,722, U.S. Pat. No. 6,368,819, U.S. Pat. No. 6,753,170 and U.S. Pat. No. 5,821,111.

In certain preferred embodiments of the invention, alcohols and acids are recovered from the fermentation broth by continuously removing a portion of the broth from the first fermentation bioreactor, separating microbial cells from the broth (conveniently by filtration), and recovering first alcohol and then acid from the broth. The alcohol may conveniently be recovered for example by distillation, and the acid may be recovered for example by adsorption on activated charcoal. The separated microbial cells are preferably returned to the fermentation bioreactor. The cell free permeate remaining after the alcohol and acid have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted during recovery of acids and/or alcohols, the pH should be re-adjusted to a similar pH to that of the broth in the fermentation bioreactor, before being returned to the bioreactor.

Where a mixed alcohol stream is recovered from one fermentation reaction, the one or more alcohols can subsequently be separated and mixed with one or more of the alcohols that is recovered from the other fermentation. In the embodiment illustrated in FIG. 1 for example, ethanol may be separated from the mixed alcohol stream of the second fermentation and pooled with ethanol recovered from the first fermentation.

Once recovered from the first fermenter, by-products such as acetate and butyrate, may be fed to the second fermenter using any standard methods or apparatus. The by-products may be fed in a batch, fed batch or continuous manner to the second fermenter. By-products such as acetate and butyrate may be added to the second fermenter in any appropriate concentration or amount as will be appreciated by skilled person. However, by way of example, acetate and/or butyrate may be added to a concentration of approximately 0.1 to approximately 10 g/L of fermentation broth, more preferable approximately 0.1 to approximately 5 g/L of fermentation broth.

The gaseous by-products produced by the second fermentation can be captured and fed to the first fermentation by any known process. However, by way of example gas may be extracted in a batch or continuous manner from the headspace of the second fermentation and fed to the first reaction in a batch, fed batch or continuous manner at a desired rate. The gas recovered from the second fermentation may be fed directly to the first fermenter or alternatively, could be combined with a gaseous substrate comprising-CO and then fed to the first fermenter. Gaseous by-products may be introduced to the first fermenter in any appropriate concentration or amount as will be appreciated by skilled person. However, in a preferred embodiment, hydrogen gas is introduced to a concentration of approximately 1% to approximately 50% by volume (of total gas volume), more preferably approximately 1% to approximately 25%, and carbon dioxide gas may be introduced to a concentration of approximately 5% to approximately 20%, more preferably approximately 5% to approximately 15%.

The invention will now be described in more detail with reference to the following non-limiting examples.

EXAMPLES

Example 1

The aim of the following set of experiments was to demonstrate that acetate, a co-product formed during microbial gas-to-ethanol production with gas mixtures lacking hydrogen, could be used as a co-substrate in a second microbial system that produced hydrogen. The effect of acetate addition as a co-substrate increases the volume of alcohol (measured as butanol) production in the hydrogen producing culture. The hydrogen, when recycled to a gas-to-ethanol production unit, resulted in improved gas-to-ethanol performance.

The research goal was to demonstrate that the acetate co-product could be used as a co-substrate, with glucose in the production of alcohol, primarily butanol, in a fermentation that produced hydrogen gas as a co-product, and the hydrogen could be used to improve the gas-to-ethanol reaction with *Clostridium autoethanogenum* growing on otherwise hydrogen-free gas mixtures. Acetate was added to serum bottle cultures of *Clostridium acetobutylicum* culture, and the degradation of acetate and production of butanol was measured over time. After a defined culture period, headspace gas collected from cultures of *Clostridium acetobutylicum* was pumped into the headspace of reaction vessels containing *Clostridium autoethanogenum* and the effect on ethanol production determined.

The benefit of effecting a linkage between processes for the production of ethanol from gases containing CO and processes for the production of mixed alcohols from sugars is demonstrated. Acetate, a by product of processes for the production of ethanol from gases containing CO can be used as a substrate allowing enhanced butanol production in a process for producing mixed alcohols from sugars. Gases produced as a result of mixed alcohol production from sugars can in turn be used to obtain increased levels of ethanol production from CO.

Methods

Growth of *Clostridium acetobutylicum* strain P262 (accession no. DSM 13864, DSMZ, Germany) involved methods familiar to those experienced in the art of using this bacterial species. Cells were maintained in 15 ml Hungate tubes in 5 mL of media with 10 mL headspace on basal media (details below) containing acetate at concentrations of either 1.7 g/l and 3.7 g/l for 8 days at 37° C.

Samples of culture media were taken at regular intervals. Cells were maintained in 15 ml Hungate tubes in 5 mL of media with 10 mL headspace. Hungate tubes were gas tight with all additions of media, gases and culture through the use of syringes and needles.

To determine the impact of evolved hydrogen gas, 50 ml cultures under a $CO_2$ gas head space in sealed 234 ml serum bottles were grown and maintained. Gas, evolved as a result of production of alcohol by *Clostridium acetobutylicum* P262 was displaced from the serum bottle with culture media and collected in evacuated serum bottles with a background $CO_2$.

| Base media used to grow *Clostridium acetobutylicum* P262 | |
|---|---|
| Media Component | Concentration per 1.0 L of Media |
| D Glucose | 50.0 g |
| Yeast extract | 5.00 g |
| Ammonium acetate | 2.00 g |
| L-cystenine | 0.50 g |
| NaCl | 1.00 g |
| $K_2HPO_4$ | 0.75 g |
| $KH_2PO_4$ | 0.75 g |
| $MgSO_4$ | 0.20 g |
| $MnSO_4 \cdot 7H_2O$ | 0.01 g |
| $FeSO_4 \cdot 7H_2O$ | 0.01 g |
| Deionised $H_2O$ | To 1 L |

Growth of *Clostridium autoethanogenum* (accession no. DSM 10061, DSMZ, Germany) was undertaken using methods previously described (Phillips, Klasson, Clausen and Gaddy, *Applied Biochemistry and Biotechnology*, 39/40 pp 559-571 (1993)).

| Media Composition for *Clostridium autoethanogenum* | |
|---|---|
| Media (LM23) Component | Concentration per 1.0 L of Media |
| $MgCl_2 \cdot 6H_2O$ | 0.5 g |
| NaCl | 0.2 g |
| $CaCl_2$ | 0.2 g |
| 100 mM sodium phosphate buffer | 160 ml |
| $NH_4Cl$ | 0.6 g |
| 85% $H_3PO_4$ | 0.05 ml |
| KCl | 0.15 |
| Composite trace metal solution (LSO6) | 10 ml |
| Composite B vitamin Solution (LS03) | 10 ml |
| Resazurin (1000 mg/L stock) | 1 ml |
| $FeCl_3$ | 0.0025 g |
| Cystine HCL | 0.75 g |
| Distilled water | To 1 litre |

| Media Composition for *Clostridium autoethanogenum* | |
|---|---|
| | per L of Stock |
| Composite B vitamin Solution (LS03) | |
| Biotin | 20.0 mg |
| Folic acid | 20.0 mg |
| Pyridoxine hydrochloride | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Litre |
| Composite trace metal solution (LSO6) | |
| Nitrilotriacetic Acid | 1.5 g |
| $MgSO_4 \cdot 7H_2O$ | 3.0 g |
| $MnSO_4 \cdot H_2O$ | 0.5 g |
| NaCl | 1.0 g |
| $FeSO_4 \cdot 7H_2O$ | 0.1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 g |
| $CuCl_2 \cdot 2H_2O$ | 0.02 g |
| $AlK(SO_4)_2 \cdot 12H_2O$ | 0.02 g |
| $H_3BO_3$ | 0.30 g |
| $NaMoO_4 \cdot 2H_2O$ | 0.03 g |
| *$Na_2SeO_3$ | 0.02 g |
| *$NiCl_2 \cdot 6H_2O$ | 0.02 g |
| *$Na_2WO_4 \cdot 6H_2O$ | 0.02 g |

*Clostridium autoethanogenum* cells were maintained in 234 ml serum bottles in 50 mL of media with 184 mL headspace. Serum bottles were gas tight with all additions of media, gases and culture through the use of syringes and needles. Serum bottles were continuously agitated to increase gas-to-liquid mass transfer.

Acetate, Butanol and Ethanol Determinations:

Gas Chromatograph HP 5890 series II—Utilizing a flame ionization detector (FID), removable, deactivated glass, injection port liner, associated regulators, gas lines, and septa.

Capillary GC Column EC1000-Alltech EC1000 30 m×0.25 mm×0.25 um column Autoinjector HP 7673A.

The Gas Chromatograph was operated in Split mode with a total flow of hydrogen of 50 mL/min with 5 mL purge flow (1:10 split), a column head pressure of 10 PIS resulting in a linear velocity of 45 cm/sec. The temperature program was initiated at 60 degrees C., hold for 1 minute then ramped to 170 degrees at 30 degrees per minute, then held for 3 minutes. This resulted in a total run time of 11.8 minutes. Injector temperature was 180 degrees and the detector temperature was 225 degrees.

Reagents used were Propan-1-ol-Reagent grade. Scharlau AL0437, Min assay by GC 99.5%; Butanol, Ethanol absolute-Scharlau ET0015, Min assay by GC 99.9; Acetic acid 100% glacial-BDH 100015N, Min assay by GC 99.8%; Orthophosphoric acid-BDH 294214Q, Min assay by GC 99.0%; Nitrogen—BOC Oxygen Free-GC make up gas; Hydrogen—BOC Oxygen Free-GC carrier gas and FID fuel; Zero air-FID oxidant; Water-deionized.

Results

Impact of Acetate on Alcohol Production by *Clostridium acetobutylicum* P262 Cultures An experiment was performed to determine the impact of acetate on butanol production, when added at various initial concentrations to batch fermentations of *Clostridium acetobutylicum* P262 over time.

Three concentrations of acetate in the initial inoculum media of a *Clostridium acetobutylicum* P262 culture were contrasted to determine the impact of acetate as a co-substrate in the production of butanol. For each initial acetate concentration ten Hungate tubes were prepared. Cultures containing initial acetate concentrations of, 1.7 g/l and 3.7 g/l were compared over 7 days.

Figure 2:
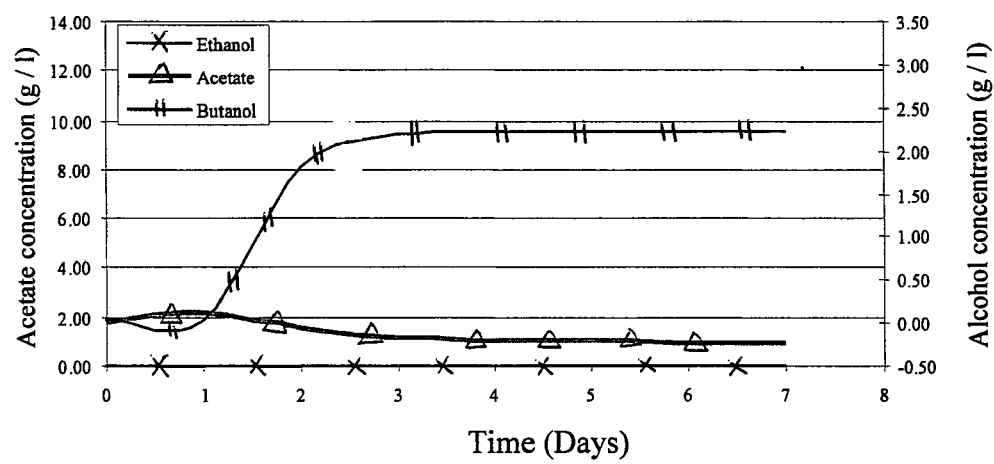
FIG. 2: Production of butanol and ethanol by *Clostridium acetobutylicum* P262 in media containing an initial concentration of acetate of 1.7 g/l acetate.
Figure 3:
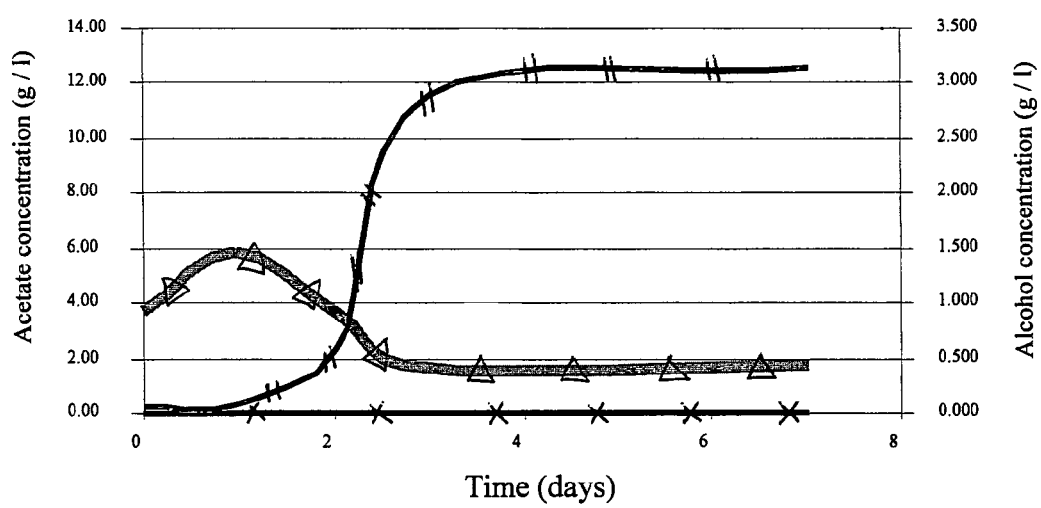
FIG. 3: Production of butanol and ethanol by *Clostridium acetobutylicum* P262 in media containing an initial concentration of acetate of 3.7 g/l acetate.

The results, depicted in FIGS. 2 and 3, indicate that an increased level of butanol production over the culture period is correlated with an increased initial concentration of acetate in the culture media. Acetate concentrations in the media were observed to fall over the culture period in correlation with butanol production.

Impact of Headspace Gases from *Clostridium acetobutylicum* Cultures on *Clostridium autoethanogenum* Cultures To determine the impact of gases evolved by a fermentation to produce mixed alcohols, 50 ml cultures of *Clostridium acetobutylicum* P262 under an initial gas headspace of $CO_2$ in sealed 234 ml serum bottles were grown and maintained for 7 days. Gas, evolved as a result of production of alcohol by *Clostridium acetobutylicum* was displaced from the serum bottle with culture media and collected in evacuated serum bottles with a gas background of $CO_2$. Established, 50 ml *Clostridium autoethanogenum* cultures were in sealed 234 ml serum bottles in the presence of the following gases at 37° C. for 3 days:

| Headspace gas | Abbreviation |
| --- | --- |
| 100% $CO_2$ at 35 psig | $CO_2$ |
| 95% CO/5% $CO_2$ at 35 psig | CO |
| Headspace gas collected from a *Clostridium acetobutylicum* culture. Gas was injected into the evacuated headspace with a background gas of $CO_2$. Headspace gas pressure was adjusted to 35 psig with $CO_2$ | ABE |

Ethanol and acetate production by *Clostridium autoethanogenum* cultures was measured using a Hewlett Packard 5890 (II) Gas chromatograph. The results are presented in FIG. 4.

Figure 4:
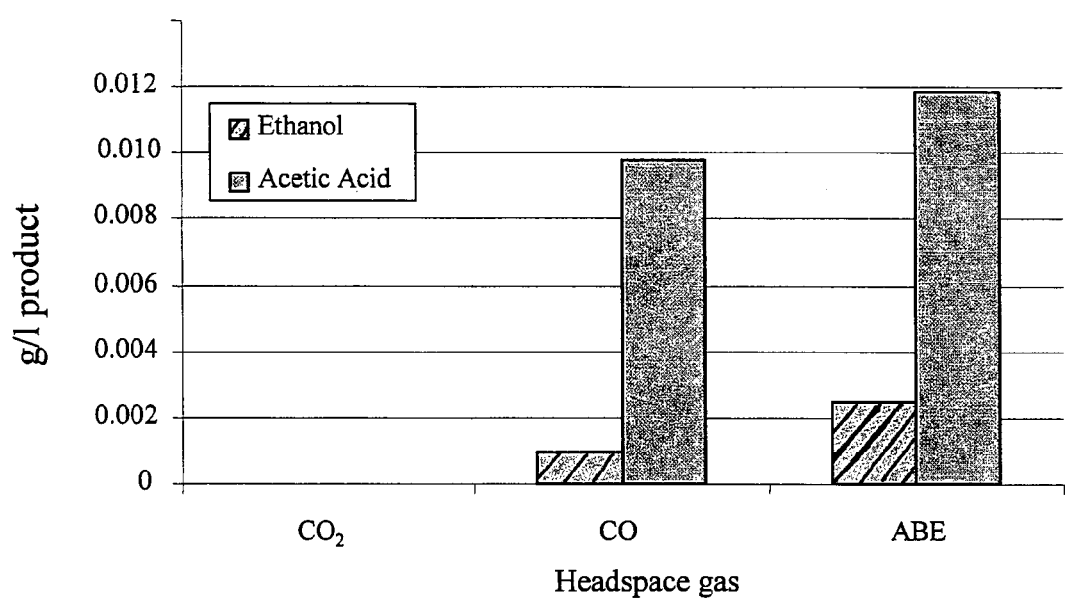
FIG. 4: Production of ethanol and acetate (product) by *Clostridium autoethanogenum* cultures after 3 days incubation in the presence of different headspace gases.

The results shown graphically in FIG. 4 contrast the production of ethanol and acetate by cultures incubated with a culture headspace containing either $CO/CO_2$ (CO), $CO_2$ ($CO_2$) with those incubated with gases evolved by the *Clostridium acetobutylicum* culture plus $CO_2$ (ABE gas) under the conditions used. When incubated in the presence of ABE gas, *Clostridium autoethanogenum* cultures produced elevated levels of both acetic acid and ethanol as compared to cultures incubated with a headspace containing CO gas. In addition, the ratio of these produced (ethanol and acetate) was observed to be altered in favour of ethanol production in cultures that were incubated in the presence of ABE gas. In the case of cultures that were incubated in the presence of ABE gas the ethanol:acetate ratio was 0.4, while in cultures that were incubated in the presence of CO the ethanol:acetate ratio was 0.1. No ethanol or acetate was produced by control cultures incubated with a headspace of $CO_2$ alone.

Example 2

The aim of the following experiment was to demonstrate that: 1) butyrate formed during microbial fermentation of a carbon monoxide containing substrate, could be used as a co-substrate in a second microbial system that produced hydrogen; and/or, 2) butyrate and acetate, co-products formed during microbial fermentations of a substrate to ethanol and/or butanol, could both be used as co-substrates in a second microbial system that produced hydrogen. The effect of butyrate, or butyrate and acetate, addition as co-substrate(s) increases the volume of butanol production in the hydrogen producing culture.

Methods

Growth of *Clostridium acetobutylicum* strain 824 (accession no. DSM 792, DSMZ, Germany) involved methods familiar to those experienced in the art of using this bacterial species. Cells were maintained in 234 ml serum bottles in 50 mL of media with 184 mL headspace on basal media containing butyrate, or acetate and butyrate, at increasing concentrations ranging from 0 to 2.6 g/l for acetate and 0 to 2.3 g/l for butyrate for 5 days at 35° C.

| Base media used to grow *Clostridium acetobutylicum* 824 | |
| --- | --- |
| Media Component | Concentration per 1.0 L of Media |
| D Glucose | 50.0 g |
| Yeast extract | 5.00 g |
| Ammonium chloride | 2.00 g |
| L-cystenine | 0.25 g |
| NaCl | 1.00 g |
| $K_2HPO_4$ | 0.75 g |
| $KH_2PO_4$ | 0.75 g |
| $MgSO_4$ | 0.20 g |
| $MnSO_4 \cdot 7H_2O$ | 0.01 g |
| $FeSO_4 \cdot 7H_2O$ | 0.01 g |
| Deionised $H_2O$ | To 1 L |

Samples of culture media were taken at regular intervals. Serum bottles were gas tight with all additions of media, gases and culture through the use of syringes and needles.

Acetate, butyrate, butanol and ethanol determinations were determined using HPLC and/or GC as follows:

HPLC

HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for sample preparation: 400 μl, of sample+50 μL of 0.15M $ZnSO_4$+50 μL of 0.15M $Ba(OH)_2$ into an eppendorf tube. Centrifuge 10 min at 12,000 rpm, 4° C. Transfer 200 μL supernatant into an HPLC vial and inject into the HPLC instrument 5 μL.

Gas Chromatography

Gas Chromatograph HP 5890 series II utilizing a flame ionization detector (FID). Capillary GC Column: EC1000-Alltech EC1000 30 m×0.25 mm×0.25 um. The Gas Chromatograph was operated in Split mode with a total flow of hydrogen of 50 mL/min with 5 mL purge flow (1:10 split), a column head pressure of 10 PIS resulting in a linear velocity of 45 cm/sec. The temperature program was initiated at 60° C., hold for 1 minute then ramped to 170° C. at 30° C. per minute, then held for 3 minutes. This resulted in a total run time of 11.8 minutes. Injector temperature was 180° C. and the detector temperature was 225° C.

Method for sample preparation: Centrifuge 500 μL sample for 10 min at 12,000 rpm, 4° C. Transfer 25 μL supernatant into an GC vial containing 450 μL water and 25 μl of internal standard spiking solution (10 g/L propan-1-ol, 5 g/L iso-butyric acid, 650 mM phosphoric acid). Inject 1 μL into the GC instrument.

Results
Impact of Butyrate or Butyrate and Acetate on Alcohol Production by *Clostridium acetobutylicum* Cultures An experiment (see FIG. 5) was performed to determine the impact of butyrate or acetate and butyrate on butanol production, when added at various initial concentrations to batch fermentations of *Clostridium acetobutylicum* 824 over time.

The culture not spiked with acetate nor butyrate produces low final concentration of butanol (0.6 g/l) and a final overpressure in the headspace of 26 psig. When increasing amounts of butyrate (from 0.8 g/l to 2.3 g/l) are added at the start of the culture, increasing amounts of butanol (1 g/l to 1.5 g/l) and gas (overpressure increases from 27 psig to 34 psig) is produced. This indicates that increasing amounts of Hydrogen and Carbon dioxide gas are being produced. Ethanol final concentration remains unchanged. Similar results are obtained when spiking the culture with increasing amounts of a mixture of acetate and butyrate: there is an increased butanol production (67 to 150% increase for butanol production compared to unspiked culture) and enhanced Hydrogen and Carbon dioxide gas production (from 26 psig overpressure for the unspiked control to a maximum 42 psig overpressure for the culture spiked with 2.6 g/l acetate and 2.1 g/l butyrate).

The results, depicted in FIG. 5, indicate that an increased level of butanol production over the culture period is correlated with an increased initial concentration of butyrate and/or butyrate and acetate in the culture media.

Example 3

The following experiment was designed to demonstrate that: 1) the addition of hydrogen gas could be used to improve the gas-to-ethanol reaction with *Clostridium autoethanogenum* growing on a substrate containing carbon monoxide; and, 2) the addition of hydrogen gas could be used to improve the gas-to-butyrate reaction with *Clostridium tetanomorphum* (DSM 528) growing on a substrate containing carbon monoxide.

Methods

Growth of *Clostridium autoethanogenum* was undertaken as per example 1. *Clostridium tetanomorphum* (DSM 528) cells were maintained in maintained in 234 ml serum bottles in 50 mL of media (media as per example 1 for *Clostridium autoethanogenum*, supplemented with 1 g/l Yeast Extract) with 184 mL headspace (95% CO in $CO_2$, 30 psig overpressure). Serum bottles were gas tight with all additions of media, gases and culture through the use of syringes and needles. Serum bottles were continuously agitated to increase gas-to-liquid mass transfer.

Acetate, butyrate, butanol and ethanol determinations were determined using methodology and apparatus as per Example 2.

Results
Impact of Hydrogen on Product Formation in the Fermentation of a Carbon Monoxide Containing Substrate by *Clostridium tetanomorphum* and *Clostridium autoethanogenum* Cultures An experiment (see FIG. 6) was performed to determine the impact of Hydrogen, when added at various initial concentrations to batch fermentations of *Clostridium autoethanogenum*, on acetate and ethanol production from a Carbon monoxide containing substrate, over time.

Hydrogen gas was added into the headspace of serum bottles at the start of the carbon monoxide containing substrate fermentation to reach a final overpressure of 30 psig and a gas composition of 17% CO, 5% $CO_2$ and increasing hydrogen concentration from 0% (Hydrogen partial pressure of 0.0 psig) to 13.7% (Hydrogen partial pressure of 6.1 psig).

By the end of the experiment all the CO gas supplied at the start of the culture was depleted, except for the control culture not spiked with hydrogen gas. The unspiked control shows low ethanol specific production of 1.2 gram per gram of cell dry weight (g/g CDW). When increasing amounts of hydrogen are spiked in the headspace of the cultures, there is an increase of acetate (to 14.5 g/g CDW) and ethanol specific production (to 4.7 g/g CDW). When comparing the partial pressure of hydrogen gas at the start and end of the experiments, a decrease can be observed, suggesting that a level of hydrogen is consumed in all cases where hydrogen is available. These results show that the presence of hydrogen in the headspace strongly promotes ethanol production and allows the full utilisation of the CO gas in the headspace.

A further experiment (see FIG. 7) was performed to determine the impact of hydrogen, when added at the start of a batch fermentations of *Clostridium tetanomorphum*, on butyrate production from a carbon monoxide containing substrate, over time. Two different gases were tested; one containing 95% CO in $CO_2$ and another containing 20% $H_2$, 20% CO and 8% $CO_2$ in $N_2$.

At the end of the fermentation, the culture containing hydrogen shows enhanced butyrate specific production (from 1.9 to 4.8 g/g CDW).

Taken together, examples 2 and 3 demonstrate the benefit of effecting a linkage between processes which produce the likes of one or more of acetate, ethanol, butyrate and/or butanol from CO containing gases and processes for the production of alcohols from sugars. In particular, butyrate or butyrate and acetate produced from fermentation on gases containing CO can be used as a substrate allowing enhanced butanol production in a process for producing mixed alcohols from sugars. Gases produced as a result of mixed alcohol production from sugars can in turn be used to obtain increased levels of ethanol, acetate, and butyrate. The inventors also believe such gases can be used to obtain increased levels of butanol in those bacterial cultures adapted to produce butanol from gaseous substrates containing CO.

The specific methods and compositions described herein are representative of preferred embodiments and are exemplary and not intended as limitations on the scope of the invention. Other objects, aspects and embodiments will occur to those skilled in the art upon consideration of this specification, and are encompassed within the scope and spirit of the invention. It will be readily apparent to one skilled in the art that varying substitutions and modifications may be made to the invention disclosed herein without departing from the scope and spirit of the invention. The invention illustratively described herein suitably may be practised in the absence of any element or elements, or limitation or limitations, which is not specifically disclosed herein as essential. Thus, for example, in each instance herein, in embodiments or examples of the present invention, the terms "comprising", "including", "containing" etc are to be read expansively and without limitation.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in New Zealand or any other country.

The invention claimed is:

1. A process for producing one more alcohols, the process comprising:
   a. in a first bioreactor, carrying out a first fermentation of a gaseous substrate that comprises CO and a gaseous co-substrate, wherein the first fermentation produces a first fermentation broth comprising one or more acids and optionally one or more alcohols;
   b. passing at least a portion of the one or more acids to a second bioreactor;
   c. in the second bioreactor, carrying out a second fermentation of a substrate comprising a carbohydrate, wherein the second fermentation produces a second fermentation broth comprising one or more alcohols, and wherein at least a portion of the one or more acids is utilised in the second fermentation to produce a gaseous co-substrate;
   d. passing at least a portion of the gaseous co-substrate produced in step (c) to the first bioreactor, wherein at least a portion of the gaseous co-substrate is utilized as a co-substrate in the first fermentation.

2. The process of claim 1 further comprising recovering at least a portion of the one or more products from one or both of the fermentations, wherein the one or more products are selected from the group comprising of: (i) the one or more acids of step (a); (ii) the one or more alcohols of step (a); and (iii) the one or more alcohols of step (c).

3. The process of claim 1 wherein the one or more alcohols comprises ethanol.

4. The process of claim 1 wherein the one or more acids comprises acetate.

5. The process of claim 1 wherein the one or more acids is selected from the group consisting of butyrate and lactic acid.

6. The process of claim 1, wherein the one acid produced in the first fermentation is acetate, and wherein at least a portion of the acetate is utilized in the second fermentation to produce a gaseous co-substrate including one or both of $H_2$ and $CO_2$.

7. The process of claim 1 wherein the first fermentation is carried out by one or more anaerobic bacteria.

8. The process of claim 7 wherein the anaerobic bacteria is selected from the group consisting of *Clostridium, Moorella, Oxobacter, Peptostreptococcus, Acetobacterium, Eubacterium, Desulfotomaculum, Archaeglobulus* and *Butyribacterium*.

9. The process of claim 8, wherein the anaerobic bacterium is *Clostridium autoethanogenum*.

10. The process of claim 1, wherein the second fermentation is carried out by one or more bacteria of the genus *Clostridium*.

11. The process of claim 10, wherein the bacterium is *Clostridium acetobutylicum*.

12. The process of claim 1, wherein the gaseous substrate is a waste gas obtained from an industrial process.

13. The process of claim 12, wherein the industrial process is selected from the group consisting of ferrous metal products manufacturing, non-ferrous products manufacturing, petroleum refining processes, gasification of biomass, gasification of municipal waste, gasification of coal, electric power production, carbon black production, ammonia production, methanol production and coke manufacturing.

14. The process of claim 1 wherein the gaseous substrate comprises less than about 15% $H_2$, less than about 10% $H_2$, or less than 5% $H_2$.

15. The process of claim 1 wherein the gaseous substrate comprises about 70% CO to about 95% CO by volume.

16. The process of claim 1 further comprising continuously removing a portion of the first or second fermentation broth and recovering separately the one or more alcohols or the one or more acids from the removed portion of the fermentation broth.

* * * * *